US005785842A

United States Patent [19]

Speck

[11] Patent Number: 5,785,842
[45] Date of Patent: Jul. 28, 1998

[54] CORROSION PROTECTION MONITORING AND ADJUSTMENT SYSTEM

[76] Inventor: Robert M. Speck, 1102 Sycamore, Richmond, Tex. 77469

[21] Appl. No.: 619,125

[22] Filed: Mar. 20, 1996

Related U.S. Application Data

[63] Continuation-in-part of Ser. No. 422,799, Apr. 17, 1995, abandoned.

[51] Int. Cl.$^6$ .................................................. G01N 27/26
[52] U.S. Cl. .................... 205/777.5; 205/776; 205/724; 205/730; 204/196; 204/197; 204/404; 340/856.3; 340/500; 340/505; 340/517; 340/645
[58] Field of Search .................................. 204/196, 197, 204/404; 205/775.5, 724, 730, 776; 340/856.3, 500, 505, 517, 645

[56] References Cited

U.S. PATENT DOCUMENTS

| | | | |
|---|---|---|---|
| 5,133,081 | 7/1992 | Mayo | 455/18 |
| 5,306,414 | 4/1994 | Glass et al. | 204/404 |
| 5,350,494 | 9/1994 | Brummelhuis | 204/196 |

*Primary Examiner*—Bruce F. Bell
*Attorney, Agent, or Firm*—Vinson & Elkins L.L.P.

[57] ABSTRACT

A system for monitoring and alternatively adjusting the electrical energy input and output of remotely located corrosion protection rectifiers on a section of a longer pipeline includes three elements. The first element is a monitoring unit which monitors electrical input, output voltage, output amperage and level of applied cathodic protection of the electrical energy provided to the pipeline by a rectifier. This data on electrical energy is then transmitted to the second element, a low-level communication satellite. The low-level communication satellite then retransmits the data to the third element, a management data center. The information received at the management data center may be monitored, recorded or transformed into adjustment signals which are then retransmitted via the low-level communication satellite back to the rectifier on the pipeline.

15 Claims, 1 Drawing Sheet

CORROSION PROTECTION MONITORING AND ADJUSTMENT SYSTEM

This is a continuation-in-part of U.S. patent application Ser. No. 08/422,799, filed Apr. 17, 1995 now abandoned.

BACKGROUND OF THE INVENTION

The present system pertains to monitoring systems; more particularly, the present system pertains to monitoring systems for distributive cathodic corrosion protection systems used in pipelines.

It has long been known that if a small direct electrical current is applied to a metallic object in a corrosive environment, both the onset and the progress of corrosion of the metallic object is inhibited. This corrosion delay or corrosion protection principle has been applied to metallic pipelines. Because of its effectiveness, government regulations now require that an electrical corrosion protection system be used on pipelines such as those pipelines which carry natural gas all over the United States.

In an ideal world, electrical pipeline corrosion protection would be effected by a large source of electrical energy placed on one end of a pipeline. This large source of electrical energy would cause sufficient electrical energy to pass through the entire pipeline to protect it against corrosion. In practice, however, the utilization of a single electrical energy source for corrosion protection of a long pipeline is impractical. Therefore, instead of using a single source of electrical energy, a series of rectifiers, which convert commonly available alternating current to more usable direct current, are placed at intervals along the length of a pipeline. A corrosion protection system which uses a plurality of rectifiers distributed over the length of a pipeline is referred to as "distributive cathodic corrosion protection."

Each rectifier provides direct current electrical energy to a section of the pipeline. The use of a plurality of individual rectifiers at intervals spread all along the length of the pipeline assures that the entire length of the pipeline bears a small electrical charge. This small electrical charge inhibits both the onset and the progress of corrosion of the metallic pipe sections which make up a long pipeline.

To ensure the effectiveness of a distributive cathodic corrosion protection system installed on a pipeline, it is necessary to periodically monitor and check the electrical energy output characteristics and performance of each individual rectifier located over the length of the pipeline.

Such periodic monitoring and checking of the electrical energy output characteristics and performance of individual rectifiers can be done physically by sending a person to the location of each rectifier and taking direct readings of various electrical output and performance measurements. Alternatively, the monitoring and checking of rectifier output has been accomplished by including a small data transmission device with each individual rectifier. The small data transmission device sends signals based on the electrical energy output characteristics of each individual rectifier to a central monitoring location. The central monitoring location then records and monitors the operation and condition of an entire array of individual rectifiers at regular intervals or even continuously.

Communications systems that have been used to send the electrical output information from the small data transmission device have included RF transmission, hardwire telephone lines and, more recently, cellular telephone systems.

While cellular telephone system transmission of rectifier output and performance is adequate in many ways, it still has some drawbacks. Specifically, all pipeline rectifiers are not located in cellular telephone coverage areas. This is because only about 85 percent of the continental United States is presently accessible by cellular telephone. While cellular telephone coverage may increase in future years, it is anticipated that there will still always be a small part of the United States where cellular telephone coverage is not available. If an individual pipeline rectifier is located in an inaccessible area, such individual rectifier must still be physically checked. Physical checking of a rectifier is both inconvenient and expensive. Additionally, if the pipeline rectifier is physically checked by a technician, human error may result in disconnecting a wire or breaking a connection. Such inadvertent acts may render the rectifier inoperative and may not be discovered until the next physical check.

While cellular telephone communication has provided an effective avenue for short-range data transmission, the reliability and dependability of cellular telephone communication is oftentimes somewhat less than desired when longer distances are involved. Further, cellular telephone communication may be rendered ineffective in certain situations ... specifically, near large trees, buildings or mountains. There is, therefore, a need in the art to provide a system for monitoring the electrical output and performance characteristics of an array of pipeline rectifiers wherein the reliability and dependability of the communication means for transmitting and receiving the operational data is increased.

In addition to the problems with cellular telephone communication systems, available designs for electrical current monitoring systems only allow for monitoring the output and condition of the pipeline rectifier. If more sophisticated electrical testing of corrosion protection systems on pipelines is required, such as momentarily shutting down major sections of the cathodic protection system and then measuring the residual electrical charge imparted to the pipeline from the array of rectifiers, it is necessary to do special custom physical, on-site programming of the remote rectifier monitoring units. Such custom, on-site programming is required because there is no existing system by which individual pipeline rectifiers can be cycled off simultaneously so that a measurement of residual electrical charge in the pipeline can be made before turning the rectifiers [taken and then cycled] back on to re-energize the distributive cathodic corrosion protection system.

One attempt at monitoring corrosion, as distinguished from corrosion protection, has been described in U.S. Pat. No. 5,306,414. Such system is based on the monitoring of electrochemical corrosion sensors, not on the monitoring of remote pipeline corrosion prevention rectifiers.

There remains, therefore, a need in the art to provide a communication system for use in a distributive cathodic corrosion protection system wherein communication with monitoring units for remote individual pipeline corrosion prevention rectifiers is continually available irrespective of the location of the rectifier. Additionally, such communication system should also provide for adjustment of the electrical operating parameters of each individual rectifier, should such be necessary.

SUMMARY OF THE INVENTION

The corrosion protection monitoring and adjustment system of the present invention provides a system for continuous worldwide communication for distributive cathodic corrosion protection systems irrespective of the location of the rectifier.

The system of the present invention for obtaining information from and adjusting the corrosion protection provided by the individual pipeline rectifiers of the present invention consists of three elements.

The first element is a remote pipeline rectifier monitoring unit. The remote pipeline rectifier monitoring unit includes a remote pipeline rectifier which supplies direct current to a section of pipeline, thus enabling the cathodic protection of the pipeline section against corrosion. The remote pipeline rectifier monitoring unit also includes a data acquisition system which monitors the electrical input to the rectifier in kilowatt-hours, and the output amperage, voltage and level of applied cathodic protection provided to the pipeline section by the rectifier. The electrical data from the data acquisition system is first coupled with a signal identifying the specific remote pipeline rectifier and then transformed into a signal easily transmitted by a modem. A transceiver, once having received the electrical signal from the modem, transmits the electrical data provided by the data acquisition system to the second element of the system of the present invention.

The second element of the system of the present invention is a low-level communication satellite which receives signals from the transceiver in the remote pipeline rectifier monitoring unit. The low-level communication satellite retransmits the signals received from the remote pipeline rectifier monitoring unit to the third element.

The third element is a computerized management data center which monitors the output of each individual rectifier and, thus, the condition of the entire length of protected pipe.

It is also possible to reverse the direction of the signal sent between the elements of the foregoing system. By reversing the direction of the signal, it is possible to create a signal at the management data center which will adjust the electrical output of the remote pipeline rectifier. This return signal is then transmitted to the low-level satellite, which retransmits it to the individual remote monitoring unit. The transceiver within the remote pipeline monitoring unit receives the correction signal and then transforms it into a signal which adjusts the operational parameters of the rectifier, and thus adjusts the electrical energy supplied to the pipeline.

BRIEF DESCRIPTION OF THE FIGURE

A better understanding of the corrosion protection monitoring and adjustment system of the present invention may be had by reference to the figure wherein.

DESCRIPTION OF THE EMBODIMENTS

Figure 1:
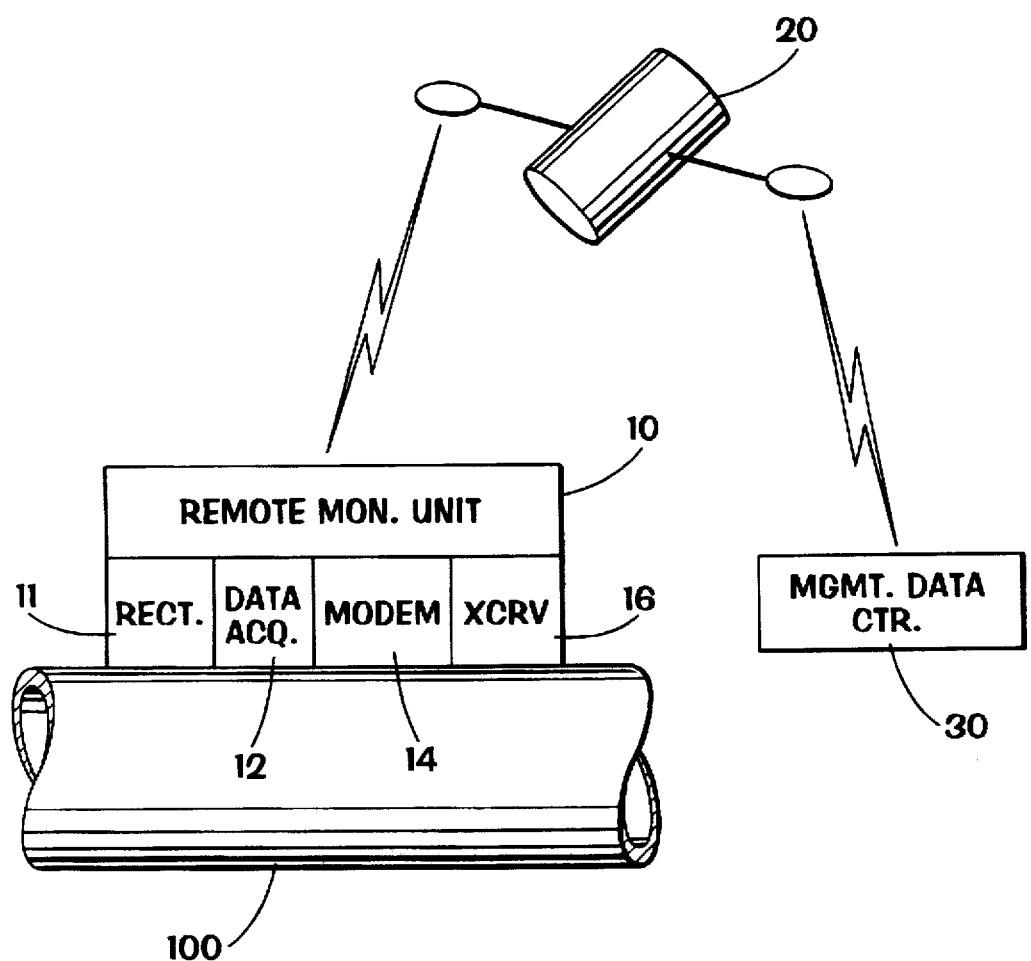
FIG. 1 is a schematic representation of the system of the present invention.

A system for measuring, monitoring and adjusting remotely located pipeline rectifiers is depicted in FIG. 1. Therein, it will be seen that a remote pipeline rectifier monitoring unit 10 preferably consists of three elements. The first element is a pipeline rectifier 11 which receives commercially available alternating electrical current and supplies low-level direct electrical current to a section of a pipeline 100. Input to the rectifier of alternating current is expressed in kilowatt-hours. The output of electrical energy [output parameters of] from the pipeline rectifier 11 is [are] expressed in terms of current flow or amperage, electrical potential or voltage and polarity. The operating parameters of the remote pipeline rectifier are fed to a data acquisition system 12 within the remote pipeline rectifier monitoring unit 10. The data acquisition system 12 then transforms the rectifier's kilowatt-hour input and the output in terms of amperage, voltage and polarity into electrical signals. The electrical signals are then fed into a modem 14 which further transforms the signals so that they may be transmitted by a transceiver 16. The transceiver 16 sends the signals to the second element of the present invention, a low-level communication satellite 20.

Low-level communication satellites such as the ones presently used by the ORBCOMM Company are placed into orbit around the earth at an altitude of approximately 40 to 50 miles. The earth is ringed by these low-level communication satellites so that signal sending units such as the remote pipeline rectifier monitoring units 10 described above will always have the ability to communicate with these low-level satellites 20 and will never be blocked from transmitting or receiving a signal because of the curvature of the earth or structures such as trees, buildings or mountains.

The signal received by the low-level communication satellite 20 is then retransmitted to the third element of the present invention, a management data center 30. The signals received at the management data center may indicate that the remote pipeline rectifier monitoring unit 10 is not operating properly or not supplying the required electrical energy to the pipeline 100. A[n] [error] signal indicating that the use of input current or that the flow of output current is outside of normal limits may indicate that there is something wrong with the remote pipeline rectifier monitoring unit 10 or that a repair or adjustment is required.

Periodically, it is also necessary to monitor the residual charge residing in a pipeline 100 after the electrical current from a rectifier is applied. To measure this residual charge, it is necessary to momentarily interrupt the flow of electrical current from a contiguous series of pipeline rectifiers. Without current flow, the pipeline, if properly protected from corrosion, should retain a small electrical charge. This electrical charge may be measured to determine the effectiveness of the cathodic protection system. Shortly after the measurement is taken, the cathodic protection system is re-energized and adjustments made where necessary. The measurement data of residual charge can be transmitted by the system of the present invention. Also, the signals to stop the flow of electrical current and to restart, or adjust the flow, may be sent from the management data center to the remote pipeline rectifiers via the satellite system 20.

It is also possible to adjust the output of electrical energy supplied by the pipeline rectifiers 10 to the pipeline 100. Such adjustment is effected by transforming any sensed errors in electrical energy output into an adjustment signal. This adjustment signal is retransmitted from the management data center 30 to the low-level satellite 20. The low-level satellite 20 then retransmits this adjustment signal to the remote monitoring unit 10, where the necessary adjustments are made to the rectifier entirely without human intervention. Verification of the implementation of adjustments can be made by noticing corresponding changes in both the electrical input to and the electrical output from the rectifier.

If desired, the signal from the remote pipeline rectifier monitoring unit 10 may be encrypted before it leaves the remote monitoring unit 10 on its way to the low-level satellite 20. Once retransmitted from the low-level satellite 20 to the management data center 30, the signal may be decoded into a usable signal. Similarly, if adjustment signals are sent, it is possible to encrypt the signal as it leaves the management data center 30 and passes through the low-level satellite 20 on its way back to the remote monitoring unit 10.

While the foregoing system has been described by reference to the preferred embodiment, it will be understood by those of ordinary skill in the art that the invention is not to be limited by the foregoing disclosure, but is to be limited only by the scope and meaning of the appended claims.

I claim:

1. A method for obtaining information describing the corrosion protection status of a section of a pipeline provided with a rectifier electrically connected to said section of a pipeline, said method comprising the steps of:

measuring the current input and output, electrical potential, and level of applied cathodic protection of the electrical energy provided by the rectifier to the section of a pipeline;

transmitting said measurements of current input and output, electrical potential and level of applied cathodic protection to a low-level communication satellite;

retransmitting the measurements received by said low-level communication satellite to a management data center.

2. The method as defined in claim 1 further including the step of encrypting said transmitted signal from said rectifier.

3. A method for obtaining electrical output information from a remote pipeline rectifier, said method comprising the steps of:

monitoring the electrical current supplied to the remote pipeline rectifier;

monitoring the output amperage, output voltage and level of applied cathodic protection of the electrical energy supplied by the remote rectifier to the pipeline;

transforming said electrical current input and said output amperage, output voltage and level of applied cathodic protection into a transmittable signal;

transmitting said signal to a low-level communication satellite;

retransmitting the measurements received by said low-level communication satellite to a management data center.

4. The method as defined in claim 3 further including the step of encrypting said transmitted signal from said rectifier.

5. A method for obtaining electrical output information from a remote pipeline rectifier, said method comprising the steps of:

acquiring data on electrical input, output amperage, output voltage and level of applied cathodic protection from the remote pipeline rectifier;

transforming said data into a transmittable signal;

transmitting said signal to a low-level communication satellite;

retransmitting said signal to a management data center.

6. The method as defined in claim 5 further including the step of encrypting said transmitted signal.

7. A system for monitoring the effectiveness of distributive cathodic protection of a pipeline comprising:

at least one rectifier for providing electrical energy to a pipeline;

means for acquiring electrical signal information associated with said electrical energy provided to the pipeline;

means for transmitting said electrical signal information to a low-level satellite;

means for retransmitting said electrical signal information to a management data center.

8. The system as defined in claim 7 further including means for encrypting said electrical signal transmitted to said low-level satellite.

9. A method for measuring the residual charge in a section of a pipeline having a corrosion protection system including a plurality of pipeline rectifiers which supply a continuous flow of electrical current to a section of the pipeline, said method comprising the steps of:

interrupting the flow of electrical current to a contiguous series of pipeline rectifiers covering a section of the pipeline;

measuring the residual charge in said section of the pipeline;

resuming the continuous flow of electrical current to said contiguous series of pipeline rectifiers covering a section of the pipeline;

transforming said measurement of the residual charge into a transmittable signal;

transmitting said transmittable signal to a low-level communication satellite;

retransmitting said signal to a management data center.

10. The method as defined in claim 9 further including the step of encrypting the transmittable signal.

11. A method for adjusting the corrosion protection of a section of a pipeline provided by a rectifier electrically connected to said section of a pipeline, said method comprising the steps of:

measuring the electrical input, output current flow, the output electrical potential, and the level of applied cathodic protection of the electrical energy provided to the section of the pipeline by the rectifier;

transmitting said measurements of electrical input, output current flow, output electrical potential and level of applied cathodic protection to a low-level communication satellite;

retransmitting said measurements received by said low-level communication satellite to a management data center;

comparing said measurements at said management data center to a preselected set of operational standards;

determining if any differences exist between said measurements and said operational standards;

transforming said differences into adjustment signals;

transmitting said adjustment signals to said low-level satellite;

retransmitting said adjustment signals to the rectifier;

transforming said adjustment signals into changes in current flow, electrical potential and level of applied cathodic protection of the electrical energy provided to the section of the pipeline by the rectifier.

12. A method for adjusting the electrical output from a remote rectifier, said method comprising the steps of:

measuring electrical input, output amperage, output voltage and level of applied cathodic protection of the electrical energy output of the remote rectifier;

transmitting said measurements to a low-level communication satellite;

retransmitting said measurements to a management data center;

retransforming said signal into said electrical input, output amperage, output voltage and level of applied cathodic protection measurements;

comparing said measurements at said management data center to a preselected set of standard measurements;

determining if any differences exist between said measurements and said standard measurements;

transforming said differences into adjustment signals;

transmitting said adjustment signals to said low-level satellite;

retransmitting said adjustment signals from said low-level satellite to the remote rectifier;

transforming said adjustment signals into changes in electrical input, output amperage, output voltage and level of applied cathodic protection provided by said remote rectifier.

13. A method for adjusting the electrical output from a remote rectifier, said method comprising the steps of:

acquiring data on electrical input, output amperage, output voltage and level of applied cathodic protection from the remote rectifier;

transforming said data into a transmittable signal;

transmitting said signal to a low-level communication satellite;

retransmitting said signal to a management data center;

comparing said data to a preselected set of measurement standards at said management data center;

determining if any differences exist between said data and said measurement standards;

transforming said differences into adjustment signals;

transmitting said adjustment signals to said low-level satellite;

retransmitting said adjustment signals from said low-level satellite to the remote rectifier;

transforming said adjustment signals into changes in the electrical input, output amperage, output voltage and level of applied cathodic protection provided by said remote rectifier.

14. A system for adjusting the electrical output of a distributive cathodic protection of a pipeline comprising:

at least one rectifier for electrically polarizing a pipeline;

means for acquiring electrical information associated with providing cathodic protection to the pipeline;

means for transmitting said electrical information to a low-level communication satellite;

means for retransmitting said electrical information to a management data center;

means for determining if said electrical information indicates effective distributive cathodic protection of the pipeline;

transforming said differences into adjustment signals;

transmitting said adjustment signals to said low-level communication satellite;

retransmitting said adjustment signals from said low-level communication satellite to said rectifier;

transforming said adjustment signals into changes in how said rectifier electrically polarizes the pipeline.

15. A method for adjusting the residual charge in a section of a pipeline having a corrosion protection system including a plurality of rectifiers for supplying a continuous flow of electrical current to the pipe section, said method comprising the steps of:

interrupting the continuous flow of electrical current to a contiguous series of rectifiers covering a pipe section;

measuring the residual charge in said section of a pipeline;

resuming the continuous flow of electrical current to said contiguous series of rectifiers;

transforming said measurement of said residual charge into a transmittable signal;

transmitting said signal to a low-level communication satellite;

retransmitting said signal to a management data center;

comparing said measurements to a preselected set of measurement standards;

determining if any differences exist between said measurements and said measurement standards;

transforming said differences into adjustment signals;

transmitting said adjustment signals to said low-level satellite;

retransmitting said adjustment signals from said low-level satellite to one or more individual rectifiers;

transforming said adjustment signals into changes in the electrical output of said one or more individual rectifiers.

* * * * *